United States Patent
Mottes

(10) Patent No.: US 9,797,814 B2
(45) Date of Patent: Oct. 24, 2017

(54) PROBE FOR IN SITU MONITORING THE ELECTRICAL CONDUCTIVITY OF SOIL SOLUTIONS

(71) Applicant: Adi Mottes, Karkur (IL)

(72) Inventor: Adi Mottes, Karkur (IL)

( * ) Notice: Subject to any disclaimer, the term of this patent is extended or adjusted under 35 U.S.C. 154(b) by 6 days.

(21) Appl. No.: 15/147,332

(22) Filed: May 5, 2016

(65) Prior Publication Data
US 2016/0252474 A1 Sep. 1, 2016

Related U.S. Application Data

(63) Continuation-in-part of application No. 14/053,740, filed on Oct. 15, 2013, now abandoned, which is a (Continued)

(30) Foreign Application Priority Data

Jun. 12, 2011 (IL) .......................................... 213498
Mar. 1, 2012 (IL) .......................................... 218431

(51) Int. Cl.
*G01N 27/06* (2006.01)
*G01N 1/14* (2006.01)
(Continued)

(52) U.S. Cl.
CPC ............. *G01N 1/14* (2013.01); *G01N 27/048* (2013.01); *G01N 33/24* (2013.01); *G01N 2033/245* (2013.01)

(58) Field of Classification Search
CPC .......... G01N 1/14; G01N 27/06; G01N 27/07; G01N 33/24; G01N 2033/245; G01N 27/02
(Continued)

(56) References Cited

U.S. PATENT DOCUMENTS 3,376,501 A * 4/1968 Peranio ................. G01N 27/07
324/450
3,906,781 A 9/1975 Vlasblom
(Continued)

FOREIGN PATENT DOCUMENTS

CN 1222676 7/1999
CN 1361420 7/2002
(Continued)

OTHER PUBLICATIONS

Essert, et al., "Combined tensiometer-solution sampling probe", Elsevier, Soil & Tillage Research 45 (1998) pp. 299-309.
(Continued)

*Primary Examiner* — Jay Patidar
(74) *Attorney, Agent, or Firm* — Lipsitz & McAllister, LLC

(57) ABSTRACT

A probe for monitoring electrical conductivity of ground water in soil is provided. The probe includes a hollow tube that includes (a) an upper tube section with an apertured stopper, (b) a lower tube section, aligned with the upper tube section and having a porous ceramic cap for inserting into soil, and (c) a T-fitting connecting between the tube sections and having an apertured T-fitting stopper. A vacuum tube is inserted through the T-fitting stopper aperture; and a conductivity sensor electrode is inserted through the upper tube section stopper aperture. The conductivity sensor electrode includes a pair of electrode poles that are spaced apart at a distance of 3-5 mm and the distance between the conductivity sensor electrode and the hollow tube is greater than 3 mm, whereby interference by air bubbles in the ground water is mitigated.

13 Claims, 4 Drawing Sheets

Related U.S. Application Data continuation of application No. PCT/IL2012/000213, filed on May 31, 2012.

(51) Int. Cl.
*G01N 33/24* (2006.01)
*G01N 27/04* (2006.01)

(58) Field of Classification Search
USPC ............... 324/376, 347, 696, 609; 73/304 R; 204/416
See application file for complete search history.

(56) References Cited

U.S. PATENT DOCUMENTS

| | | | |
|---|---|---|---|
| 4,513,608 A | 4/1985 | Cuming | |
| 4,654,598 A * | 3/1987 | Arulanandan | G01N 27/223 324/347 |
| 5,418,466 A | 5/1995 | Watson et al. | |
| 5,558,463 A | 9/1996 | Geisel | |
| 6,521,119 B2 | 2/2003 | Krausa et al. | |
| 7,005,662 B2 | 2/2006 | Caron et al. | |
| 7,261,245 B2 | 8/2007 | Zur | |
| 7,319,332 B2 * | 1/2008 | Lenormand | G01N 33/241 324/376 |
| 7,624,630 B2 | 12/2009 | Masuda | |
| 7,956,624 B2 | 6/2011 | Beaulieu | |
| 2001/0027927 A1 | 10/2001 | Krausa et al. | |
| 2005/0177309 A1 | 8/2005 | Sri Ranjan et al. | |
| 2006/0254371 A1 | 11/2006 | Shiloni et al. | |
| 2009/0038390 A1 | 2/2009 | Dahan | |
| 2009/0107725 A1 | 4/2009 | Christy et al. | |
| 2009/0166520 A1 | 7/2009 | Tuli et al. | |
| 2009/0322357 A1 | 12/2009 | Beaulieu | |
| 2011/0012627 A1 * | 1/2011 | Dukhin | G01N 15/088 324/699 |

FOREIGN PATENT DOCUMENTS

| | | |
|---|---|---|
| CN | 101144788 | 3/2008 |
| CN | 101526446 | 9/2009 |
| CN | 101706381 | 5/2010 |
| DE | 19748124 | 3/1999 |
| DE | 10058416 | 2/2002 |
| FR | 1070566 | 7/1954 |
| JP | S6466554 | 3/1989 |
| WO | 97/42494 | 11/1997 |
| WO | 00/33071 | 6/2000 |
| WO | 2007/128122 | 11/2007 |

OTHER PUBLICATIONS

"Combined tensiometer-soil solution sampler", retrieved from the Internet, [date unavailable]:<URL:http//hopmans.lawr.ucdavis.edu/2_multi_functional_probes.htm>.

* cited by examiner

PROBE FOR IN SITU MONITORING THE ELECTRICAL CONDUCTIVITY OF SOIL SOLUTIONS

CROSS-REFERENCE TO RELATED PATENT APPLICATIONS

This application is a Continuation-in-Part (CIP) of U.S. Ser. No. 14/053,740 filed on 15 Oct. 2013, which is a continuation of International Patent Application PCT/IL2012/000213 filed on 31 May 2012, claiming the benefit of Israeli patent application no. 213498 filed on 12 Jun. 2011 and Israeli patent application no. 218431 filed on 1 Mar. 2012, each of which is incorporated herein by reference in their entirety.

FIELD OF THE INVENTION

The present invention relates to monitoring of chemical and physical properties of soil solutions. More specifically, the present invention relates to a probe and method for direct monitoring electrical conductivity (EC) of soil solution.

BACKGROUND OF THE INVENTION

The activity and productivity of agricultural crops are strongly influenced by the level of salinity, i.e. by the total dissolved solids in the soil solution, which is easily determined by electric conductivity measurements.

The ability of most crops and plants to draw and extract soil water containing fertilizer by means of the roots depends on the salinity level of the soil solution. The higher the salinity or the electrical conductivity, the lower the absorbance of the soil solution by the plant. Therefore, accurate measurement of the level of salinity of the soil solution is decisive in agriculture. Namely, monitoring of the electrical conductivity of the soil solution is highly essential for setting proper treatment scheduling, for deciding when to irrigate, how much water and fertilizer to use and where they should be applied.

Devices for measuring soil properties are disclosed in U.S. Pat. No. 4,513,608, which describes a moisture sensing assembly constructed with different zones of porous material; U.S. Pat. No. 5,418,466, which discloses a sensor use for salinity measurement using an oscillating tuned circuit; US 2009/0038390, which discloses a vadose zone probe mounted on an inflatable sleeve; US 2009/0166520, which discloses an in-situ probe 5 having a plunger inserted in the probe; and U.S. Pat. No. 3,906,781, which discloses a soil probe for measuring soil pressure.

CN 1361420 relates to a probe with an electrode lead of ion meter connected with ion selective electrode sealed in a porous pottery clay cup in the bottom of probe and connected to an automatic controller via a guide pipe. The drawback of this probe 10 is the small and narrow inner space of the pottery clay which is not able to hold an EC electrode and to manage electrical conductivity tests.

DE 10058416 discloses a probe and method for determining oxygen content of interstitial water in formations containing sediment and clay. The probe has a very small outer diameter of 5-6 mm and even smaller inner diameter of 2-3 mm which allows the insertion of only a sensor. A vacuum is pulled through the side of the tube. The drawback of such a probe is as follows: the extremely narrow inner diameter of 2-3 mm is able to hold only an electrode with very little free space. The very narrow tube may be advantageous for oxygen measurement but not for measuring electrical conductivity. The reason being, that air bubbles enter the tube with soil solution and adhere to the walls of the tube and/or the electrode and in such a narrow tube the bubbles stay there without rising to the surface of the liquid. Such air bubbles distort EC measurement.

The above references all describe devices and methods for direct monitoring of ground water properties in the soil. These devices and methods may be suitable for monitoring a large number of soil properties such as pH, phosphorus, ammonium, magnesium, chlorides, nitrates, potassium, water hardness, or other soil properties but can produce inaccurate measurements or no readings at all for Electrical Conductivity (EC) since EC is highly sensitive to continuity disturbances in the ground water solution. Every change in the volume and direction of the flow of the water as a result of irrigation or rainfall may cause the creation of a temporary physical state of lack of homogeneity in the ground structure. This, in turn, includes the formation of air pockets which disturb the EC measurements. Such a situation gets worse when the water content in the ground is low, and as a result the electrodes lose contact with the 5 water in the soil.

There is also known the Mottes Soil Solution Extractor and the manual portable testing kits, which include a probe with a vacuum tube inserted therein, a porous ceramic cap or tip at the bottom and a syringe attached to the vacuum tube at the top. Soil solution is drawn into the probe through the porous ceramic cap by vacuum created by the syringe. Once the soil solution is drawn inside the probe, the solution is withdrawn into the syringe outside of the probe to be checked manually by a portable EC meter and also other testing kits. This kit allows for precise testing of soil solutions in the field as conditions change over time due to fresh soil solution that is drawn in from the soil by the manual syringe operation. The Mottes extractor is accompanied by a variety of portable soil solution testing kits for chloride, nitrate, pH and Electric Conductivity (EC).

Most of the above devices have a porous ceramic section through which ions diffuse in and out of the probe. Such devices may produce correct measurements that are indicative of certain properties of the soil despite the entrapped air in the probe. However, for EC measurements, air entrapped in the ceramic section space and/or near the EC electrodes disturbs and restricts the functioning thereof and therefore, alters the measurements to be higher than normal resistance readings (lower conductivities, or even a zero reading).

As noted above, the various available devices that conduct direct monitoring of soil properties within the ground enable the measurements of numerous soil properties except for EC, as EC is highly sensitive to continuous disturbances in the ground solution medium.

To obtain proper EC readings, there must be full and complete solution (liquid) between the sensor electrodes without any intervals or disconnections, which may result from air bubbles or air pockets. Also, when the soil is relatively dry, the solution drawn into the porous ceramic cap may lack continuity, and thus, the EC electrodes may not carry out a measurement at all and may show a read error of the value "0".

In sensors for measuring soil properties other than EC, the method of sensing is based on the measurement of an ion concentration in the volume surrounding the sensor, and thus correct measurements can be obtained even if there is no perfect continuity of a solution surrounding the sensor. A pH sensor, for instance, examines 10 the ion concentration of hydrogen in the volume surrounding the sensor.

Thus, the prior art devices and methods are not suitable for conducting EC measurements that are reliable and accurate in all instances, as accurate EC measurements require a perfect continuity of the solution surrounding the sensor electrode.

It is an object of the present invention to overcome or eliminate the problems associated with the prior art devices.

More specifically, it is an object of the present invention to provide a probe that measures in situ, accurately and reliably the electrical conductivity (EC) of soil solutions (ground water).

The probe of the present invention is advantageous for obtaining continuous in-situ in-field measurements that are highly precise and reliable. Such measurements provide growers with in-depth information on fluctuations in the electrical conductivity levels which reflect the total dissolved solids in the soil solution. Thus, the growers benefit from water and fertilizer savings, as well as from a good harvest 25 with increased crops together with a reduction in groundwater pollution that keeps the environment clean and green.

SUMMARY OF THE INVENTION

The present invention provides a probe that can make electrical conductivity measurements of ground water in the field. One of the principles of obtaining such measurements that are accurate and representative is using a probe with an electrical conductivity sensor having a pair of electrode poles that are spaced apart far enough 5 so that air-bubbles will not interfere with the measurements and that allow those bubbles to be readily evacuated from the probe. Another principle is to provide an area surrounding the conductivity sensor that is suitable to allow air-bubbles to be evacuated so as not to congregate in the measurement area.

We have discovered that it is possible to introduce a vacuum tube either 10 through the side or through the top opening of the probe and maintain the vacuum tube parallel to the sensor probe. This allows for continuous monitoring of soil solution, making both, the sensor and vacuum tube an integral part of the probe. Moreover, since the sensor is maintained at all times inside the probe, the sensor is not affected by sunlight, keeping the measurements always stable and reliable. The electrodes are generally sheathed in a rigid or semi-rigid tube, approximately up to cm long.

In accordance with embodiments of one aspect of the present invention, there is provided a probe for monitoring electrical conductivity of ground water in soil. The probe includes a hollow tube that includes (a) an upper tube section stoppered at one end with a stopper having an upper tube section stopper aperture, (b) a lower tube section, aligned with the upper tube section and capped at its bottom with a porous ceramic cap configured to be insertable into soil, and (c) a T-fitting connecting between the upper tube section and lower tube section and having a T-fitting stopper with a T-fitting stopper aperture. The probe further includes a vacuum tube inserted 25 through the T-fitting stopper aperture; and a conductivity sensor electrode inserted through the upper tube section stopper aperture. The conductivity sensor electrode includes a pair of electrode poles that are spaced apart at a distance of about 3-5 mm and the distance between the conductivity sensor electrode and the hollow tube is greater than about 3 mm, whereby interference by air bubbles in the ground water is mitigated.

In some embodiments, the T-fitting stopper aperture is perpendicular to the upper and the lower tube sections. In some embodiments, the T-fitting stopper aperture is at an angle to the upper and the lower tube sections.

In some embodiments, the hollow tube of the probe has an outside diameter of about 18 to 25 mm and an inside diameter range of about 14 to 21 mm. In some embodiments, the probe is about 15 cm to 20 cm long.

In some embodiments, the conductivity sensor electrode extends down adjacent to the ceramic cap. In some embodiments, the vacuum tube extends down 10 adjacent to the ceramic cap. In some embodiments, the vacuum tube in the hollow tube is substantially parallel to the electric conductivity sensor electrode. In some embodiments, the outside diameter of the electric conductivity sensor electrode is in the range of about 6-7 mm.

In some embodiments, the vacuum tube is composed of a semi-rigid section 15 inserted into the probe and connected to a flexible section attached to a vacuum generator. In some embodiments, the semi-rigid section of the vacuum tube has an outside diameter of about 3-4 mm and the flexible section has an inside diameter of about 3-4 mm.

In some embodiments, the porous ceramic cap is configured to allow free movement of all ions in the ground solution into the tube. In some embodiments, the vacuum tube is connected to a syringe.

In some embodiments, the syringe is connected to the vacuum tube via a valve.

In some embodiments, the sensor probe is connected to a processor to monitor and transfer of measurement data.

In some embodiments, measurement data can be transferred from the sensor to the processor via wireless connection.

In accordance with the present invention, there is provided a method for monitoring of soil solution properties. The method includes the following steps: (1) providing a probe as defined above; (2) inserting the probe into the ground within the range of the irrigation means in proximity of a plant or tree roots system; (3) applying vacuum to draw ground solution into the probe to cover the EC sensor electrodes; (4) conducting measurements via the EC sensor on said solution, and (5) reading and analyzing the resulting data.

In some embodiments, the resulting data received from the EC electrode is sampled, collected and transmitted continuously.

Further aims, features and advantages of the invention will become apparent from the following detailed description taken in conjunction with the following figures.

DETAILED DESCRIPTION

Figure 1:
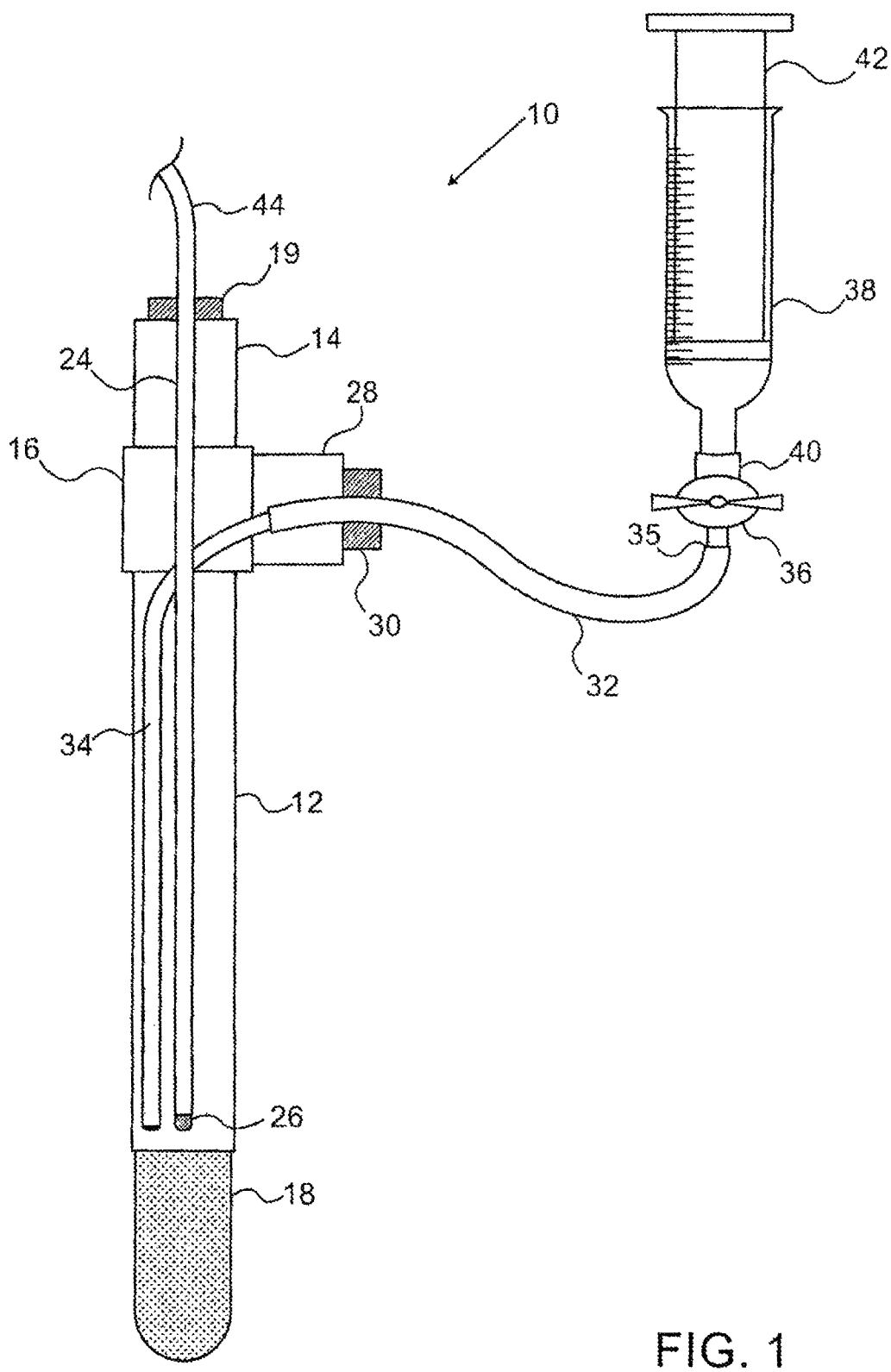
FIGS. 1-3 illustrate embodiments of a probe for direct monitoring of soil solution properties in accordance with the present invention.

FIG. 1 shows a probe 10 including a hollow tube with a lower tube section 12 and an upper tube section 14. Tube sections 12 and 14 are connected in series through a T-fitting 16 for example by hermetically gluing the sections into the T-fitting. Lower tube section 12 is capped at the bottom with a porous ceramic tip or cap 18 for inserting into soil. Upper tube section 14 is sealed at the top with a stopper 19, which has an opening through which an EC sensor probe 24 can be inserted. Sensor probe 24 has a sensor electrode 26 at its distal end, which is typically inserted down toward the bottom of lower tube section 12.

T-fitting 16 has a side aperture from which extends a tube 28 sealed (e.g. 10 glued) therein hermetically. Tube 28 is sealed with a stopper 30. A flexible vacuum tube 32 is inserted through stopper 30 and is connected hermetically to a semi-rigid inner vacuum tube 34 that extends into lower tube section 12. The other end 35 of vacuum tube 32 is connected to a valve 36 that is connected to a syringe 38 through conical tube section 40.

Semi-rigid inner vacuum tube 34 preferably has an outside diameter of about 3 mm-4 mm, and flexible outer vacuum tube 32 preferably has an inside diameter of about 3 mm to 4 mm.

Such a tubing arrangement is suitable since inner vacuum tube 34 can neither be too flexible nor too rigid in order to maneuver the angle through T-fitting 16 if inner vacuum tube 34 is to be inserted substantially down into lower tube section 12. Outer vacuum tube 32 is preferably flexible for easy manipulating and positioning of syringe 38.

A plunger 42 in syringe 38 can pull a vacuum in probe 10. It is preferable that inner vacuum tube 34 be inserted close to the bottom of lower tube section 12. This will ensure that the entire ground solution drawn into probe 10 can be withdrawn and that fresh ground solution can be drawn in.

Sensor probe 24 has the tip of sensor electrode 26 located parallel to inner vacuum tube 34 in lower tube section 12 and preferably extends its entire length (generally 12 cm) down into lower tube section 12, but may be shorter as long as it can be immersed in the soil solution. In this embodiment, probe 10 is relatively short, about 15 cm, and sensor electrode 26 extends close to the top of ceramic cap 18.

Sensor electrode 26 is an electrical conductivity (EC) sensor. Electrical conductivity measurement is very sensitive, and unlike measurements such as pH, chlorides, oxygen, nitrates, phosphorus, ammonium, water hardness, potassium, magnesium, or other soil solution properties that are not sensitive to the presence of air bubbles in the liquid media. EC measurements can not be carried out if the liquid media contains air bubbles that may accumulate around the sensor. Such air bubbles are introduced upon drawing in the ground water through ceramic cap 18. Therefore, to provide a soil solution free of air bubbles, lower tube section 12 preferably has an inner diameter wide enough to enable bubbles to rise to the top surface of the solution and not adhere to the inner walls thereof, vacuum inner tube 34 and around or between sensor electrode 26 itself, which would interfere with the EC measurement. Moreover, lower tube section 12 should be sufficiently wide to accommodate both the sensor and the vacuum tube. Therefore, in accordance with embodiments of the present invention, tube sections 12 and 14 preferably have an outside diameter of between 18-25 mm and an inside diameter of between 14-21 mm in order to accommodate sensor probe 24 and inner vacuum tube 34 side by side. In a preferred embodiment sensor probe 24 is connected to a controller (not shown) via cable 44.

Porous ceramic cap 18 is made of inert material, which is not affected by soil components such as fertilizers and allows free transfer of the ions present in the ground solution into probe 10.

Stoppers 19 and 30 can be made of rubber, plastic, cork, glass or other material able to form a tight seal. T-fitting 16 should be made from a tight fitting material to match hermetic sealing (gluing) with tube sections 12, 14 and tube 28. Syringe 38 should preferably be of sufficient volume (not less than 60 ml.) in order be able to create a vacuum of up to 0.9 bars easily.

The role of syringe 38 is two-fold: (1) to create a vacuum and draw soil solution into probe 10 to at least cover sensor electrode 26 by opening valve 36 and pulling plunger 42 outward and then closing valve 36, at which time the electrical conductivity (EC) of the solution can be measured; and (2) to transfer the soil solution from lower tube section 12 to syringe 38 by opening valve 36 and drawing the solution from the tube into syringe 38 while drawing in new fresh soil solution into probe 10 for the next measurement, then closing valve 36 and expelling the solution from syringe 38. Thus, filling and emptying of probe 10 with a refreshed ground solution can be achieved quickly and without requiring a significant period of time for the soil solution to come to equilibrium.

It should be noted that sensor probe 24 is inserted through stopper 19 of upper tube section 14 into lower tube section 12 sufficiently to have sensor electrode 26 completely immersed in the soil solution drawn into probe 10. It is desired to keep the diameter of lower tube section 12 within the limits as defined, in order to draw in soil solution and avoid air bubbles that interfere with EC measurements.

Figure 2:
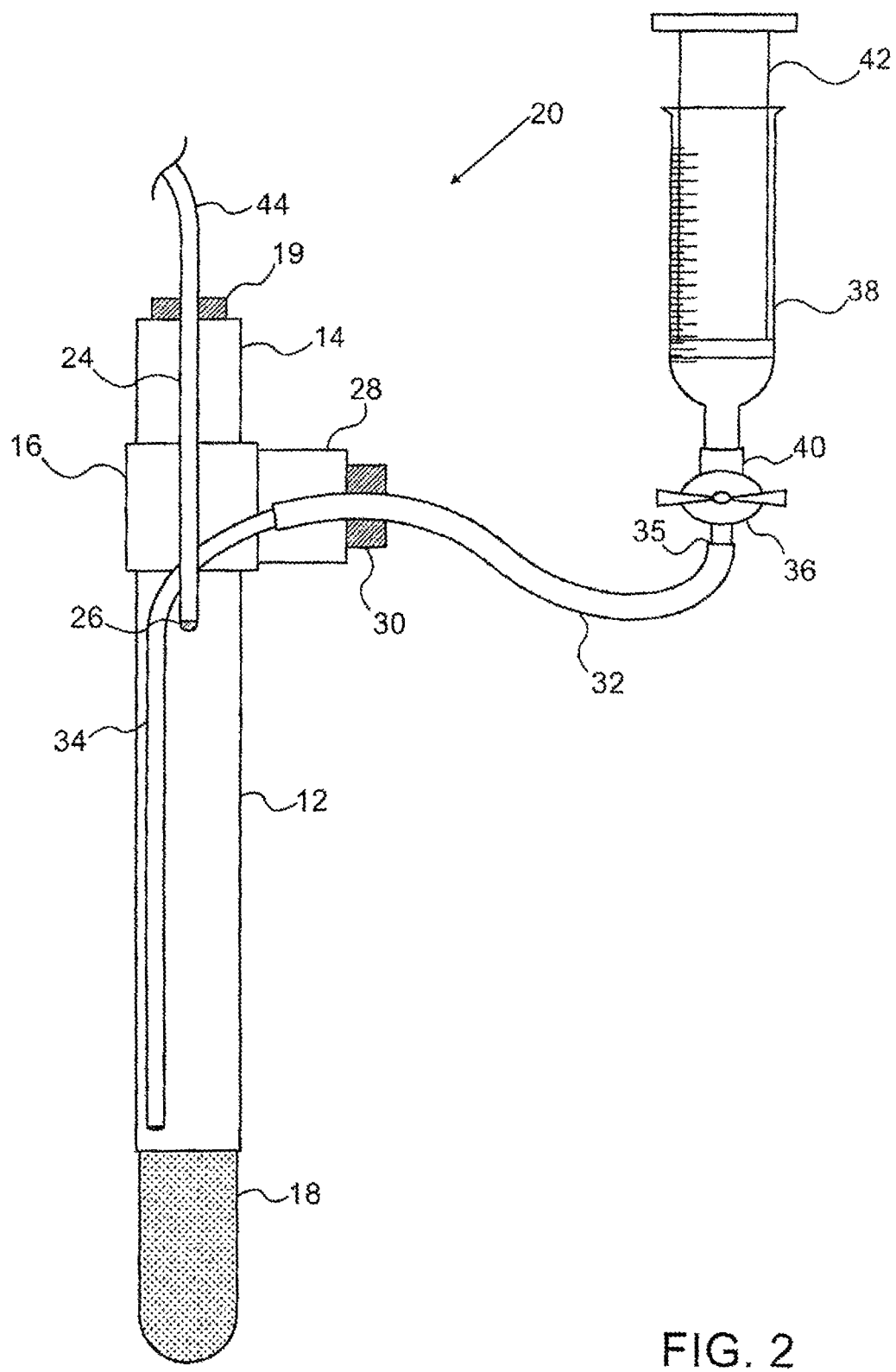

FIG. 2 illustrates another embodiment of probe 10. In this case the electric conductivity (EC) sensor probe 24 does not go to the bottom of lower tube section 12, but still can measure the electric conductivity of the soil solution since the vacuum pulled via inner vacuum tube 34 will bring the solution up in lower tube section 12 and cover sensor electrode 26, enabling correct measurement. The vacuum created by plunger 42 via syringe 38 is preferably up to about 0.9 bar as probe 10 is long and the soil solution is to be drawn up high.

Figure 3:
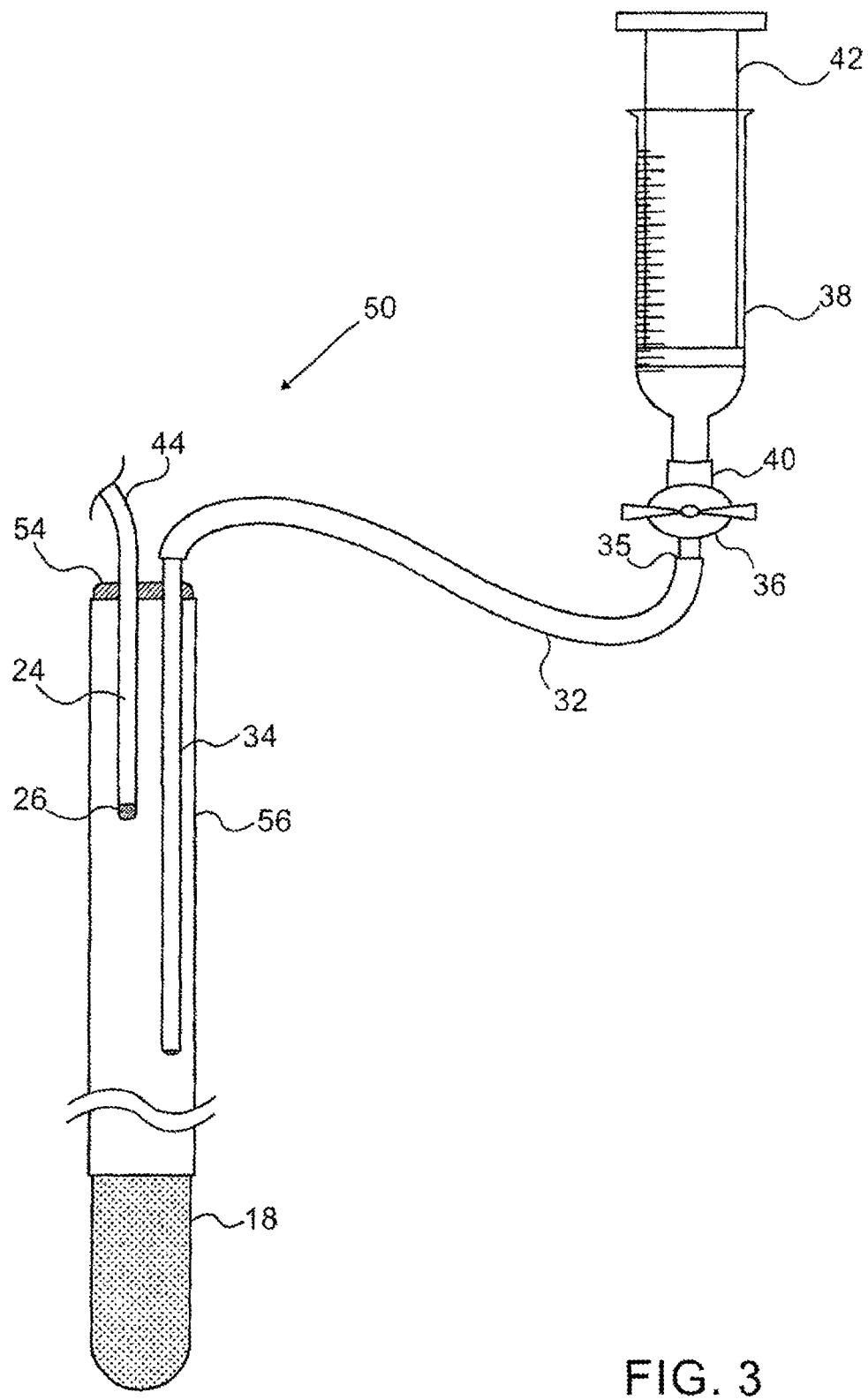

FIG. 3 shows another embodiment of probe 10, wherein both inner vacuum tube 34 and electric conductivity (EC) sensor probe 24 are introduced through a stopper 54 into a tube 56. As can be seen in FIG. 3, probe 10 can vary in length depending on the particular soil to be measured, but since (EC) sensor probe 24 is generally only about 12 cm long, the soil solution is drawn up high enough in the probe to completely cover sensor electrode 26. Inner vacuum tube 34, however, can be as long as desired; the closer it is to the bottom of the tube the easier to remove all of the soil solution from tube 56 by vacuum.

Figure 4:
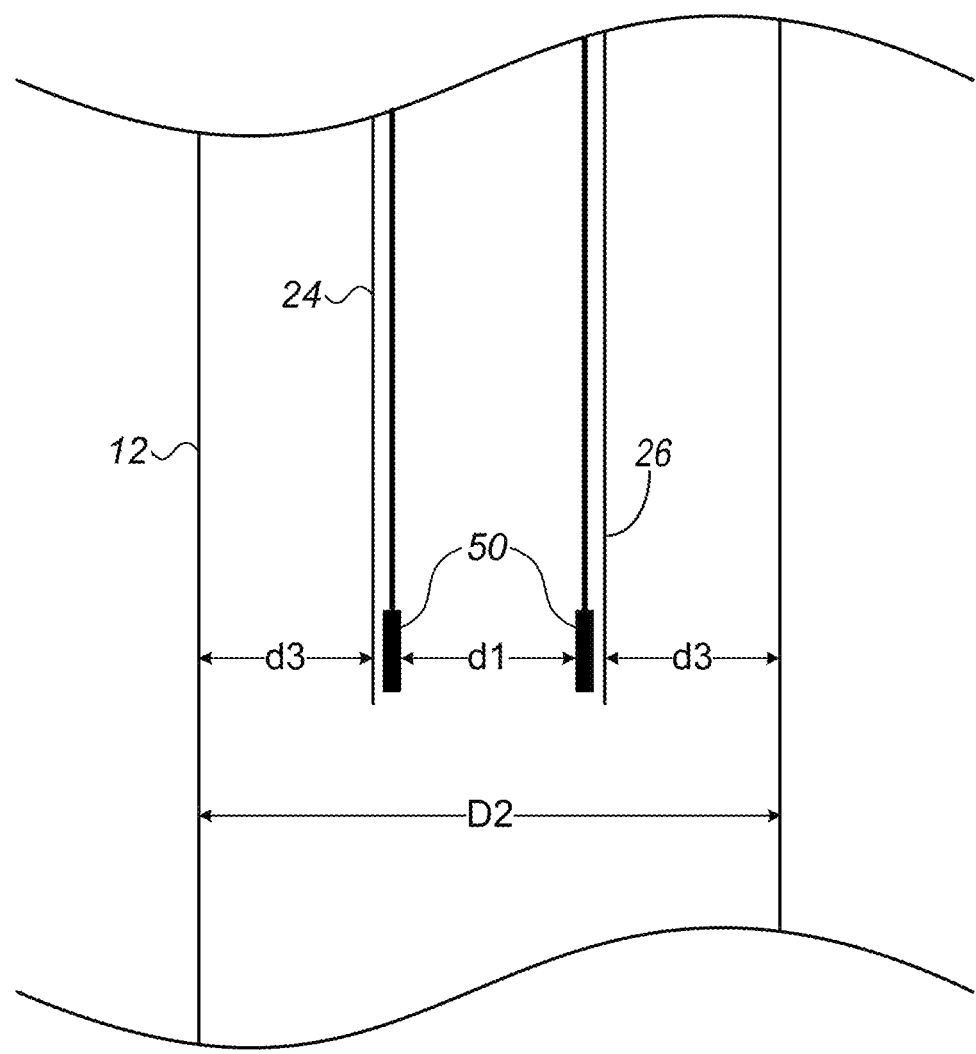
FIG. 4 is an enlarged view of the probe's electro-conductivity sensor in accordance with embodiments of the present invention.

FIG. 4 shows an enlarged view of the end of sensor electrode 26 whereby a pair of electrode poles 50 is illustrated. Poles 50 are disposed adjacent the inner walls of electrode 26 and are spaced apart at a distance dl of about 3-5 mm, whereby interference by air bubbles in the ground water is mitigated. Without limitation to theory, it is believed that due to the aforementioned spacing, any bubbles in the ground water that enter lower tube section 12 will either not enter the distal opening of electrode 26, for example a grouping of adjacent bubbles; or if a small grouping of singular bubble, those bubbles will readily exit without inappropriate interference between poles 50, whereby conductivity measurement issues are mitigated.

With respect to the annular area between conductivity sensor electrode 26 and lower tube section 12 of probe 10, the distance d3 between the outer wall of the conductivity sensor electrode and the inner wall of the lower tube section is greater than about 3 mm, whereby any bubbles that are drawn into lower tube section 12 of probe 10 can be readily evacuated from the probe via the annular area.

Operating Procedures

The operation will be discussed with reference to FIG. 1. Probe 10 operates as follows: the probe, having a suitable length for the specific soil depth is inserted into the soil to the depth desired. Initially, syringe 38 is connected to valve 36 at its connector 40 while plunger 42 is pushed in fully to the end. Valve 36 is then opened to provide a free air path from syringe 38 through vacuum tubes 32, 34 to the inner space of probe 10. Plunger 42 is then fully withdrawn to create a vacuum via vacuum tubes 32, 34 in probe 10 and valve 36 is then closed to block the path between syringe 38 and vacuum tube 32, in order to maintain the vacuum in probe 10. Syringe 38 may be disconnected from valve 36 at this time. The soil solution is thus drawn into lower tube section 12 through porous ceramic cap 18.

Since the soil solution is drawn up into lower tube section 12, the solution covers sensor electrode 26 and measurements can be made continuously.

It should be noted that syringe 38 as such, is not part of probe 10, rather an exemplary and practical means of creating a vacuum, and can be replaced by other vacuum generators.

After rain or irrigation, the relative concentrations of nutrients, fertilizers, etc. in the ground solution may vary significantly. Therefore one way of measuring electrical conductivity (EC) manually on site is as follows:

(a) Syringe 38 is connected to valve 36 with plunger 42 pushed in fully to the end.

(b) Valve 36 is set to an open position between syringe 38 and vacuum tubes 32, 34.

(c) Plunger 42 is pulled back enough to create a suitable vacuum, drawing in soil solution into lower tube section 12.

(d) Valve 36 is then closed to block the path between syringe 38 and vacuum 15 tube 32, in order to maintain the vacuum in probe 10.

(e) Syringe 38 may be disconnected from valve 36 at this time, and plunger 42 is pushed back into syringe 38.

(f) The above procedure may be repeated in order to increase the vacuum in probe 10 up to about 0.9 bars.

The solution drawn into lower tube section 12 is a representative sample of the ground solution and the first measurement may be conducted once the ground solution reaches above sensor electrode 26.

As time passes, the amount of nutrients, fertilizers and amounts of water in the ground vary and the ions will flow in and out of lower tube section 12 until equilibrium is established between the ions in the ground water (solution) and the ions in lower tube section 12. Continuous monitoring of the solution in probe 10 will provide a curve of the actual fluctuation of ion concentration in the ground solution over time.

In order to improve the equilibrium process, it is recommended to refresh the solution in probe 10 by repeating the above manual procedure, preferably once a week.

The in-situ measurements may be transmitted continuously from the EC sensor probe 24, via a cellular data-logger to an internet database server for a continuous viewing of the data which may be presented at the website in the form of a graph or table, and for generating analyses of the obtained data based on which the farmer may regulate the delivery and supply of fertilizers, nutrients and irrigation.

What is claimed is:

1. A probe for monitoring electrical conductivity of ground water in soil comprising:
    a hollow tube comprising:
        an upper tube section stoppered at one end with a stopper having an upper tube section stopper aperture,
        a lower tube section, aligned with the upper tube section and capped at its bottom with a porous ceramic cap configured to be insertable into soil and having an inner wall,
        a T-fitting connecting between the upper and the lower tube sections and having a T-fitting stopper with a T-fitting stopper aperture;
    a vacuum tube inserted through the T-fitting stopper aperture; and
    a conductivity sensor electrode inserted through the upper tube section stopper aperture and having an inside diameter and an outside diameter,
    wherein the conductivity sensor electrode is configured to be used in-situ and comprises a pair of electrode poles that are spaced apart at a distance of about 3-5 mm and the distance between an outer wall of the conductivity sensor electrode and the inner wall of the lower tube section is greater than about 3 mm, whereby interference by air bubbles in the ground water is mitigated.

2. The probe of claim 1, wherein the T-fitting stopper aperture is perpendicular to the upper and the lower tube sections.

3. The probe of claim 1, wherein the T-fitting stopper aperture is at an angle to the upper and the lower tube sections.

4. The probe of claim 1, wherein the hollow tube of the probe has an outside diameter of about 18 to 25 mm and an inside diameter range of about 14 to 21 mm.

5. The probe of claim 1, wherein the probe is between 15 cm and 20 cm long.

6. The probe of claim 1, wherein the conductivity sensor electrode extends down adjacent to the ceramic cap of the lower tube section.

7. The probe of claim 1, wherein the vacuum tube extends down adjacent to the ceramic cap of the lower tube section.

8. The probe of claim 1, wherein the vacuum tube in the hollow tube is parallel to the electric conductivity sensor electrode.

9. The probe of claim 1, wherein the outside diameter of the electric conductivity sensor electrode is in the range of about 6-7 mm.

10. The probe of claim 1 wherein the vacuum tube is composed of a semi-rigid section inserted into the probe and connected to a flexible section attached to a vacuum generator.

11. The probe of claim 10, wherein the semi-rigid section of the vacuum tube has an outside diameter of about 3-4 mm and the flexible section has an inside diameter of about 3-4 mm.

12. The probe of claim 1, wherein the porous ceramic cap is configured to allow free movement of all ions in the ground solution into the tube.

13. The probe of claim 1, wherein the vacuum tube is connected to a syringe.

* * * * *